(12) United States Patent
Nakamura

(10) Patent No.: US 10,138,025 B2
(45) Date of Patent: Nov. 27, 2018

(54) MEDICAL BAG HANDLING SYSTEM AND MEDICAL BAG HOLDING CASSETTE

(71) Applicant: TERUMO KABUSHIKI KAISHA, Tokyo (JP)

(72) Inventor: Masahiko Nakamura, Shizuoka (JP)

(73) Assignee: Terumo Kabushiki Kaisha, Tokyo (JP)

(*) Notice: Subject to any disclaimer, the term of this patent is extended or adjusted under 35 U.S.C. 154(b) by 344 days.

(21) Appl. No.: 14/779,253

(22) PCT Filed: Apr. 5, 2013

(86) PCT No.: PCT/JP2013/060485
§ 371 (c)(1),
(2) Date: Sep. 22, 2015

(87) PCT Pub. No.: WO2014/162593
PCT Pub. Date: Oct. 9, 2014

(65) Prior Publication Data
US 2016/0046410 A1  Feb. 18, 2016

(51) Int. Cl.
| | | |
|---|---|---|
| *B65D 33/14* | (2006.01) | |
| *A61M 1/02* | (2006.01) | |
| *F16B 17/00* | (2006.01) | |
| *A01N 1/02* | (2006.01) | |
| *A61J 1/16* | (2006.01) | |

(52) U.S. Cl.
CPC .......... *B65D 33/14* (2013.01); *A01N 1/0263* (2013.01); *A61J 1/16* (2013.01); *A61M 1/0286* (2014.02); *F16B 17/00* (2013.01); *A61M 1/0209* (2013.01)

(58) Field of Classification Search
CPC ....... A61M 1/0286; A01N 1/0263; A61J 1/16; B65D 33/14; F16B 17/00

USPC .................................. 248/95, 694, 40, 194
See application file for complete search history.

(56) References Cited

U.S. PATENT DOCUMENTS

| | | | |
|---|---|---|---|
| 6,910,998 B2 | 6/2005 | Eberle | |
| 2005/0018931 A1* | 1/2005 | Shrader | B65D 33/14 |
| | | | 383/23 |
| 2007/0209960 A1 | 9/2007 | Leoncavallo et al. | |

FOREIGN PATENT DOCUMENTS

| | | | | |
|---|---|---|---|---|
| FR | 2261933 A1 * | 9/1975 | | B65D 33/14 |
| JP | 11285521 A | 10/1999 | | |
| JP | 2008503321 A | 2/2008 | | |
| JP | 2012510298 A | 5/2012 | | |
| JP | 2012510299 A | 5/2012 | | |
| WO | WO2006009650 A1 | 1/2006 | | |
| WO | WO2010061863 A1 | 6/2010 | | |
| WO | WO2010061866 A2 | 6/2010 | | |

(Continued)

OTHER PUBLICATIONS

Extended European Search Report and Opinion, EPApplication No. 13881133.6, dated Nov. 21, 2016.

(Continued)

*Primary Examiner* — Gwendolyn W Baxter
(74) *Attorney, Agent, or Firm* — John R. Merkling

(57) ABSTRACT

A medical bag handling system (10) includes a plurality of cassettes (16) capable of holding bags for blood (14), and connecting means (32) capable of connecting one cassette (16) and another cassette (16). Accordingly, the cassettes (16) can be easily connected, and the plurality of bags for blood (14) supported by the respective cassettes (16) can be collectively handled.

3 Claims, 15 Drawing Sheets

(56) References Cited

FOREIGN PATENT DOCUMENTS

| WO | WO2011083120 A1 | 7/2011 |
| WO | WO2014099515 A1 | 6/2014 |

OTHER PUBLICATIONS

Japanese and English Translation for the International Search Report completed by the Japanese Patent Office for PCT Application No. PCT/JP2013/060485, dated Jul. 2, 2013, 3 pages.

* cited by examiner

MEDICAL BAG HANDLING SYSTEM AND MEDICAL BAG HOLDING CASSETTE

TECHNICAL FIELD

The present invention relates to a medical bag handling system and a medical bag holding cassette configured at the time of handling a plurality of medical bags in medical institutions.

BACKGROUND ART

In recent technologies of blood transfusion, blood component transfusion is employed, in which components of blood (whole blood) obtained from blood donation and the like are separated, and only a component necessary for a patient is supplied. The blood component transfusion enables reduction of burdens or side effects on a patient's circulatory system and efficient use of the donated blood.

In the separation of the blood components, a centrifuge machine disclosed in the specification of U.S. Pat. No. 6,910,998 centrifugally separates blood into a light supernatant (platelet poor plasma) fraction, a heavy precipitation (concentrated red blood cell) fraction, and buffy coat formed therebetween. These centrifugally separated components are transferred to and preserved in predetermined medical bags, using a blood bag system configured from a plurality of preservation bag (medical bags) and a plurality of tubes.

Incidentally, when the blood bag system is directly attached to the centrifuge machine, a plurality of medical bags and tubes may be entangled in a complicated manner, and attachment may become difficult and workability may be decreased. Therefore, the present applicant has proposed, as disclosed in JP 2012-510299 W, the medical bag in which the whole blood is stored and a part of the tubes connected to the medical bag are handled by being fixed and held to a cassette. The blood bag system is attached to the centrifuge machine through the cassette. Therefore, labor of arrangement of the bags and tubes can be substantially saved, and the blood bag system can be easily set to the centrifuge machine. Further, after centrifugal separation, the medical bags can be hung from a hanging tool or the like and caused to stand by while the medical bags and the cassette are integrated.

As described above, a handling property of the blood bag system is improved by use of the cassette. However, there are still inconvenient points for users. Specifically, when a plurality of cassettes (that is, a plurality of medical bags) is individually hung from the hanging tool, work (for example, buffy coat pooling work) in a state of hanging the cassettes (medical bags) becomes complicated, and an inconvenience of a decrease in workability is caused. Further, a larger space (work place) is required by a space of randomly arranged cassettes.

SUMMARY OF INVENTION

The present invention has been made in view of the foregoing, and an objective is to provide a medical bag handling system and a medical bag holding cassette that enable collective handling of a plurality of medical bags, and thus can improve a handling property of various types of work, using the plurality of medical bags, and achieve space saving, with a simple configuration.

To solve the problem, a medical bag handling system according to the present invention includes a plurality of medical bag holding cassettes capable of holding a medical bag, and connecting means capable of connecting one of the medical bag holding cassettes and another of the medical bag holding cassettes.

According to the above description, the medical bag handling system can connect the plurality of medical bag holding cassettes, with a simple configuration that includes the connecting means. As a result, the medical bags respectively supported by the medical bag holding cassettes can be collectively handled. For example, when the plurality of medical bags is used at the time of buffy coat pooling, these medical bags can be easily handled. Therefore, work efficiency is improved. Further, by the collective handling of the medical bag holding cassettes, a decrease in a space can be achieved, and work can be favorably performed even in a small space.

In this case, the medical bag holding cassette is formed into a box shape having a predetermined thickness and having planar portions on front and rear sides. The connecting means can have a configuration including an engaging portion that is formed on one planar portion of the medical bag holding cassette, and attachably/detachably engages the another medical bag holding cassette, and a portion to be engaged that is formed on the other planar portion at an opposite side to the one planar portion, and is attachably/detachably engaged with the medical holding cassette different from the another medical bag holding cassette.

The connecting means is configured from the engaging portion formed on the one planar portion of the medical bag holding cassette, and the portion to be engaged formed on the other planar portion at the opposite side, so that the medical bag holding cassettes can be connected and layered in a thickness direction. Accordingly, the plurality of medical bags can be arranged and connected in the thickness direction, and thus its handling can become easier.

Further, the engaging portion may be a hole portion or a recessed portion formed in the one planar portion, and the portion to be engaged may be a protruding portion formed in a protruding manner corresponding to the hole portion or the recessed portion, at an opposite side to a formed position of the hole portion or the recessed portion.

The connecting means is configured from an engagement structure of the hole portion or the recessed portion, and the protruding portion, as described above. Therefore, the medical bag holding cassettes can be brought to come close to each other in a state where the planar portions coincide with each other, whereby, the medical bag holding cassettes can be easily connected.

Alternatively, the medical bag holding cassette may be formed into a box shape having a predetermined thickness and having planar portions on front and rear sides, and the connecting means may be configured from a device that can hold the plurality of medical bag holding cassettes in a state where the planar portions face each other.

The medical bag handling system can use a conventional medical bag holding cassette as it is, by connecting the plurality of medical bag holding cassettes using the device. Therefore, an increase in cost due to preparation of new medical bag holding cassettes can be suppressed.

Further, to solve the above problem, the present invention provides a medical bag holding cassette that can hold a medical bag, in which the medical bag holding cassette is formed into a box shape having a predetermined thickness and having planar portions on front and rear sides, and the planar portion includes connecting means connectable with another medical bag holding cassette.

Accordingly, the medical bag holding cassette can be connected with another medical bag holding cassette. Therefore, a user can collectively handle the medical bags to be supported.

DESCRIPTION OF EMBODIMENTS

Hereinafter, a medical bag handling system according to the present invention will be described in detail, exemplarily using embodiments favorable in a relationship with a medical bag holding cassette that configures the medical bag handling system, with reference to the appended drawings.

The medical bag handling system according to the present invention is configured, when using a plurality of medical bags, to be able to collectively handle these medical bags. Especially, a medical bag handling system 10 according to the present embodiment illustrated in FIG. 1 can be favorably applied to work of "buffy coat pooling (hereinafter, referred to as BC pooling)" that collects buffy coat generated by centrifugal separation of whole blood into one bag. This BC pooling is performed for preparing a platelet product (blood product) with buffy coat.

Here, steps up to the BC pooling at the time of manufacturing the blood product will be schematically described. First, a blood collection step of collecting blood (whole blood) from a donor is performed. Next, a centrifugation step of centrifugally separating the collected whole blood by a blood product device 12 (centrifuge machine: see FIG. 4), and separating the whole blood into a plurality of separated sections (for example, the plasma, the buffy coat, and the concentrated red blood cells) is performed. After the centrifugation step, a transfer step of storing respective blood components centrifugally separated using the blood product device 12 in different preservation bags as they are is performed. The buffy coat is obtained by being separated after the transfer step, and the BC pooling is performed using the obtained buffy coat.

Figure 1:
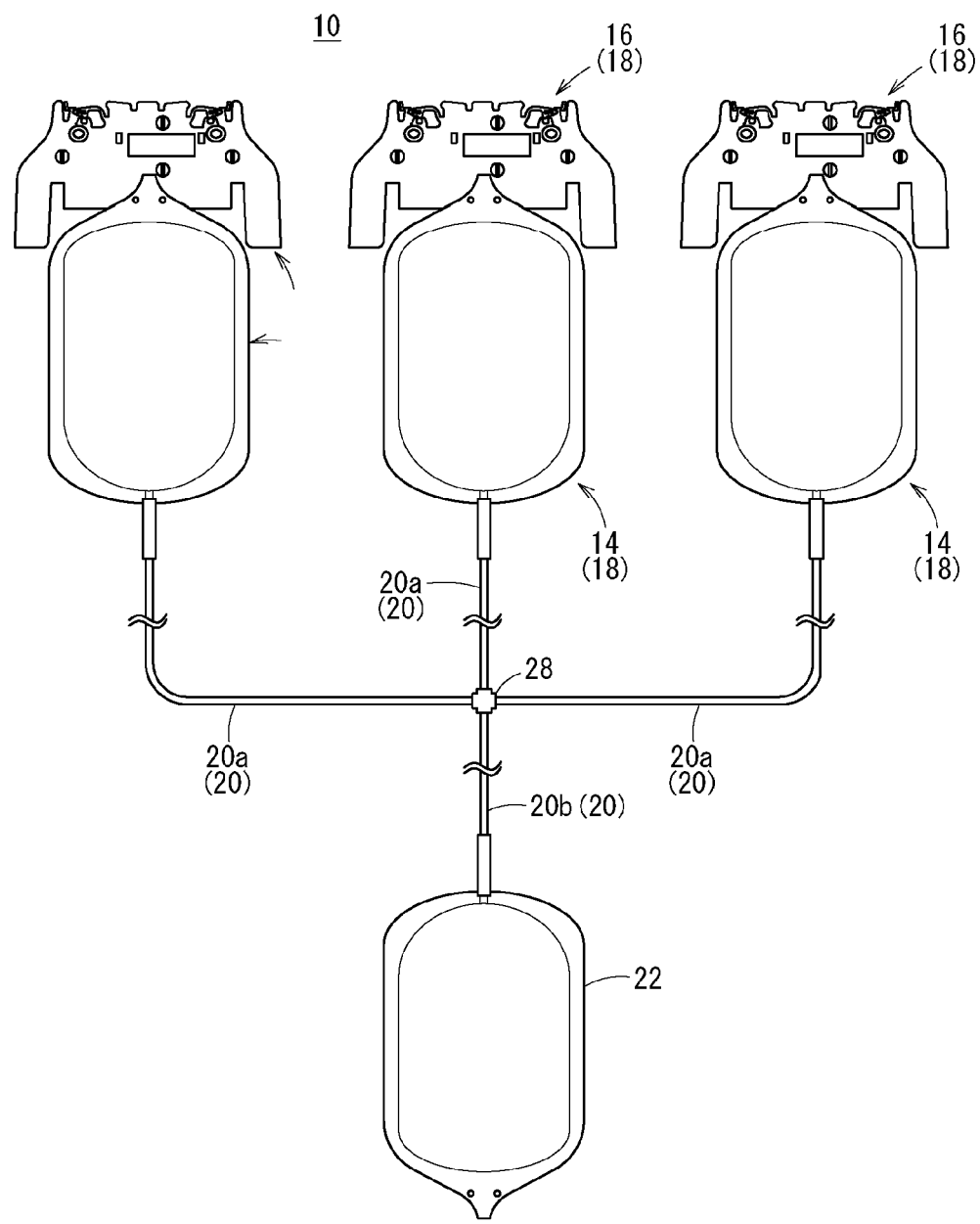
FIG. 1 is a schematic explanatory diagram illustrating an overall configuration of a medical bag handling system according to an embodiment of the present invention.

In the BC pooling, as illustrated in FIG. 1, a plurality of bags for blood 14 (medical bags) in which the buffy coat is stored is prepared, and a system of collecting the buffy coat in one buffy coat bag (hereinafter, referred to as BC bag 22) is built. The blood bag 14 in which the buffy coat is stored has a configuration of being supported by a medical bag holding cassette 16 (hereinafter, simply referred to as cassette 16). In the following description, an assembly of the blood bag 14 and the cassette 16 is called bag assembly 18.

Figure 2:
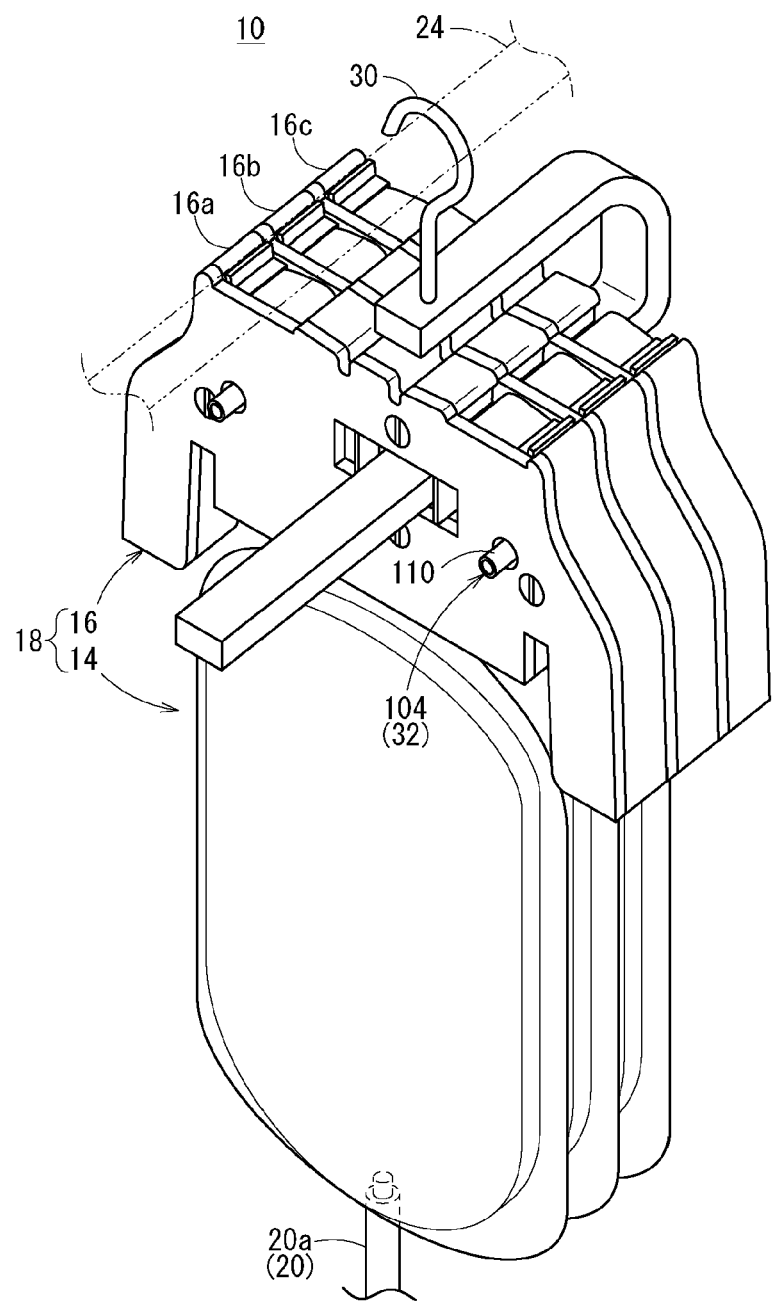
FIG. 2 is a perspective view illustrating a connection state of a bag assembly of FIG. 1.

The medical bag handling system 10 is configured as a BC pooling system, and includes a plurality of bag assemblies 18, a plurality of pooling tubes 20, a BC bag 22, and a hanging tool 24 (see FIG. 2).

Note that FIG. 1 illustrates the plurality of bag assemblies 18 being arranged, for easy understanding of the medical bag handling system 10. However, for practical purposes, the medical bag handling system 10 has a configuration in which the bag assemblies 18 are connected and integrally hung, as illustrated in FIG. 2. Further, FIGS. 1 and 2 illustrate three bag assemblies 18 (bags for blood 14). However, the number of bags for blood 14 is not especially limited, and, for example, about two to six bags for blood 14 can be used according to the amount of the buffy coat stored in the blood bag 14, and the like.

The blood bag 14 is a bag used to store and preserve the buffy coat generated by the centrifugal separation of the whole blood or blood components. The blood bag 14 serves as a part of a blood bag system 26 built for centrifugal separation before the centrifugal separation of the whole blood (in the blood collection step and the centrifugation step). Specifically, the blood bag 14 is used as a preservation bag in which the whole blood or a separated blood component obtained through blood collection from a donor is stored. That is, the blood bag 14 serves as a bag for whole blood preservation before separation and as a bag for buffy coat storage after separation.

The blood bag 14 is formed into a bag shape such that sheet materials having flexibility are layered, and peripheral sealing portions of the layered sheet materials are bonded (through thermal fusion bonding or high-frequency fusion bonding) or glued. Examples of a material that configures the sheet materials include a material made of a flexible resin such as polyvinyl chloride or polyolefin. Further, since the blood bag 14 stores the whole blood in the blood collection step, it is favorable that a blood preservation solution having a blood anticoagulant property is included in the blood bag 14. As the blood preservation solution, a blood preservation solution containing a citric acid, a phosphoric acid, and glucose (citrate phosphate dextrose (CPD)) can be favorably used.

One end portion of the pooling tube 20 (upstream-side pooling tube 20a) is connected to a lower portion of the blood bag 14. The upstream-side pooling tube 20a (and a downstream-side pooling tube 20b) include a flow path that can circulate the buffy coat.

A plurality (three) of the upstream-side pooling tubes 20a are prepared for one BC bag 22 by being connected for each bag assembly 18. The other end portions of the respective upstream-side pooling tubes 20a are connected to a connector 28 (multiport connector or a combination of several connectors), so that the respective flow paths are merged in the connector 28. Further, one end portion of the pooling tube 20 (downstream-side pooling tube 20b) connected to the BC bag 22 is connected to the connector 28. The downstream-side pooling tube 20b transfers the buffy coat merged in the connector 28 to the BC bag 22.

The BC bag 22 collectively stores the buffy coat transferred from the plurality of bags for blood 14, thereby to prepare and preserve a platelet product therein. The BC bag 22 can be configured from the material exemplified in the blood bag 14. Further, a preservation solution for platelet may be included in the BC bag 22.

In the medical bag handling system 10, the BC bag 22 and the bag assembly 18 have a configuration of being hung from the hanging tool 24 (see FIG. 2). At this time, the hanging tool 24 hangs the blood bag 14 through the cassette 16 and a hook member 30.

The cassette 16 that supports the blood bag 14 consistently supports the blood bag 14 from the blood collection step to the BC pooling. That is, the cassette 16 is essentially used to easily attach the blood bag 14 to the blood product device 12, and in the present embodiment, the cassette 16 is used to hang the blood bag 14 at the time of BC pooling.

Therefore, the cassette 16 is configured to be mounted to the blood product device 12 together with the blood bag 14, and is provided in the centrifugation step and the transfer step of the whole blood by the blood product device 12. Further, after the centrifugal separation, the cassette 16 is removed from the blood product device 12 while mounting the blood bag 14, and is hung from the hanging tool 24. The cassette 16 can be connected with another cassette 16 used for the BC pooling when being hung, as illustrated in FIG. 2, and the bag assemblies 18 can be integrally handled accordingly. At this time, the hook member 30 is favorably configured to integrally hold the connected cassettes 16. Connecting means 32 of the cassette 16 will be described in detail below.

In the following description, for easy understanding of the present invention, the respective steps (the blood collection step, the centrifugation step, and the transfer step) performed before the BC pooling will be described in relationships with the bag assembly 18 and the blood bag system 26 applied to the steps.

Figure 3:
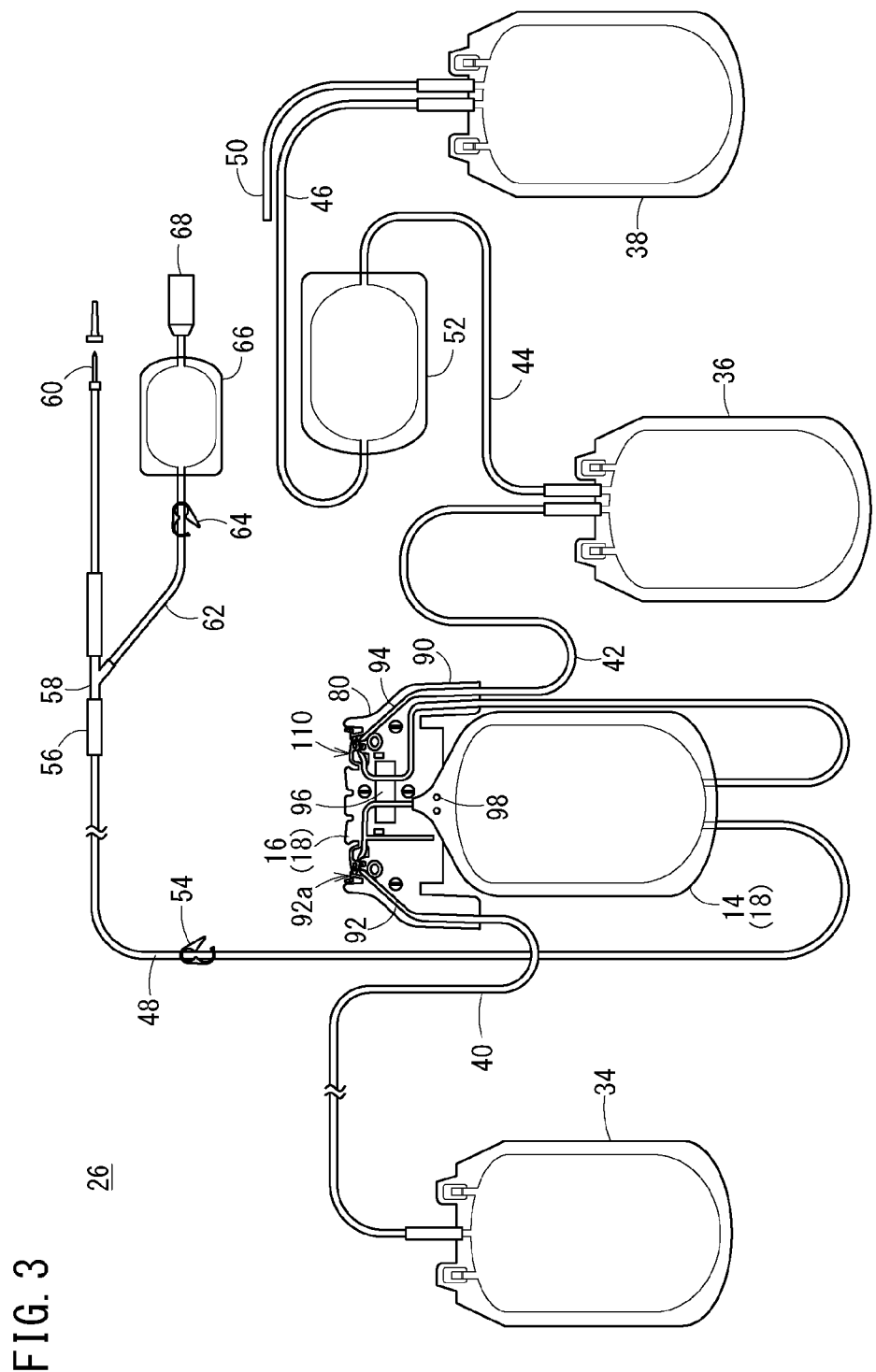
FIG. 3 is a schematic explanatory diagram illustrating an overall configuration of a blood bag system including the bag assembly of FIG. 2.

The blood bag system 26 illustrated in FIG. 3 is built to transfer and preserve the plasma (supernatant liquid) that is a centrifugally separated low specific gravity component, the buffy coat that is an intermediate specific gravity component, and the concentrated red blood cells (precipitation liquid) that is high specific gravity components. Further, in the blood bag system 26, the separated concentrated red blood cells are separated and preserved in red blood cells added to a saline adenine glucose mannitol (SAG-M) liquid (hereinafter, referred to as RC-SAGM) that is a red blood cell preservation solution, and in concentrated red blood cells (leukocyte reduced red cells concentrates, hereinafter, referred to as LR-RCC) obtained such that white blood cells are removed from the RC-SAGM.

The blood bag system 26 includes a plasma bag 34, an RC-SAGM bag 36, and an LR-RCC bag 38, as the preservation bags other than the blood bag 14. The plasma bag 34, the RC-SAGM bag 36, and the LR-RCC bag 38 can be configured from a similar material to the above-described material for the blood bag 14. The plasma bag 34 stores and preserves the plasma transferred from the blood bag 14. The RC-SAGM bag 36 stores and preserves the concentrated red blood cells transferred from the blood bag 14. The RC-SAGM bag 36 includes the SAGM that is a mixture solution containing mannitol, glucose, adenine, and sodium chloride, as the blood preservation solution having an anticoagulant property of the concentrated red blood cells, as described above. The LR-RCC bag 38 stores and preserves the LR-RCC.

The bags are connected by a plurality of tubes (first to fourth tubes 40, 42, 44, and 46) that can circulate the whole blood or the blood components. A transparent and flexible resin-made tube is applied to the first to fourth tubes 40, 42, 44, and 46 (including a blood collecting tube 48 and a sample tube 50 described below). The first tube 40 connects the blood bag 14 and the plasma bag 34, and transfers the plasma that is the low specific gravity component. The second tube 42 connects the blood bag 14 and the RC-SAGM bag 36, and transfers the concentrated red blood cells that are the high specific gravity components. The third tube 44 and the fourth tube 46 connect the RC-SAGM bag 36 and the LR-RCC bag 38, and transfers, to the LR-RCC bag 38, the concentrated red blood cells (LR-RCC) from which the white blood cells (predetermine component) have been removed with a filter 52 provided between the third tube 44 and the fourth tube 46. Further, the blood collecting tube 48 used at the time of blood collection from a donor is connected to the blood bag 14, and the sample tube 50 that can take out a part of the LR-RCC is connected to the LR-RCC bag 38 in addition to the fourth tube 46.

The blood collecting tube 48 includes a clamp 54, a sealing member 56, a three-port connector 58, and a blood collecting needle 60 in a middle of the tube 48. Further, a branch blood collecting tube 62 is connected to the three-port connector 58, and a clamp 64, an initial flow blood bag 66, and a sampling port 68 are connected to the branch blood collecting tube 62.

When the whole blood is collected from a donor, first, an initial flow (collected blood initial flow) of the collected whole blood is stored in the initial flow blood bag 66 by a predetermined amount, before the whole blood is stored in the blood bag 14. Then, a blood sampling tube (not illustrated) is mounted to the sampling port 68 connected to the initial flow blood bag 66, and the collected blood initial flow is collected in the blood sampling tube. The collected blood initial flow is used as blood for examination. After the collection of the collected blood initial flow, storage of the whole blood to the blood bag 14 is performed.

In the blood collection step, it is favorable that an upper part of the blood bag 14 is attached to the cassette 16 and is built as the bag assembly 18 in advance. The cassette 16 holds both of the first and second tubes 40 and 42 connected to the blood bag 14, thereby to easily handle the tubes near the blood bag 14. The bag assembly 18 can be easily attached to the blood product device 12 as is the state after the blood collection step. Note that the blood collecting tube 48 used in the blood collection step is sealed with a tube sealer or the like and cut out near the blood bag 14 after the blood collection step.

The blood bag system 26 configured as described above is set to the blood product device 12, and the centrifugation step and the transfer step are performed. In the centrifugation step, the whole blood stored in the blood bag 14 is separated into the plasma, the buffy coat, and the concentrated red blood cells. Then, in the transfer step, the plasma is stored in the plasma bag 34, and the concentrated red blood cells are stored in the RC-SAGM bag 36, so that the buffy coat is left in the blood bag 14.

Figure 4:
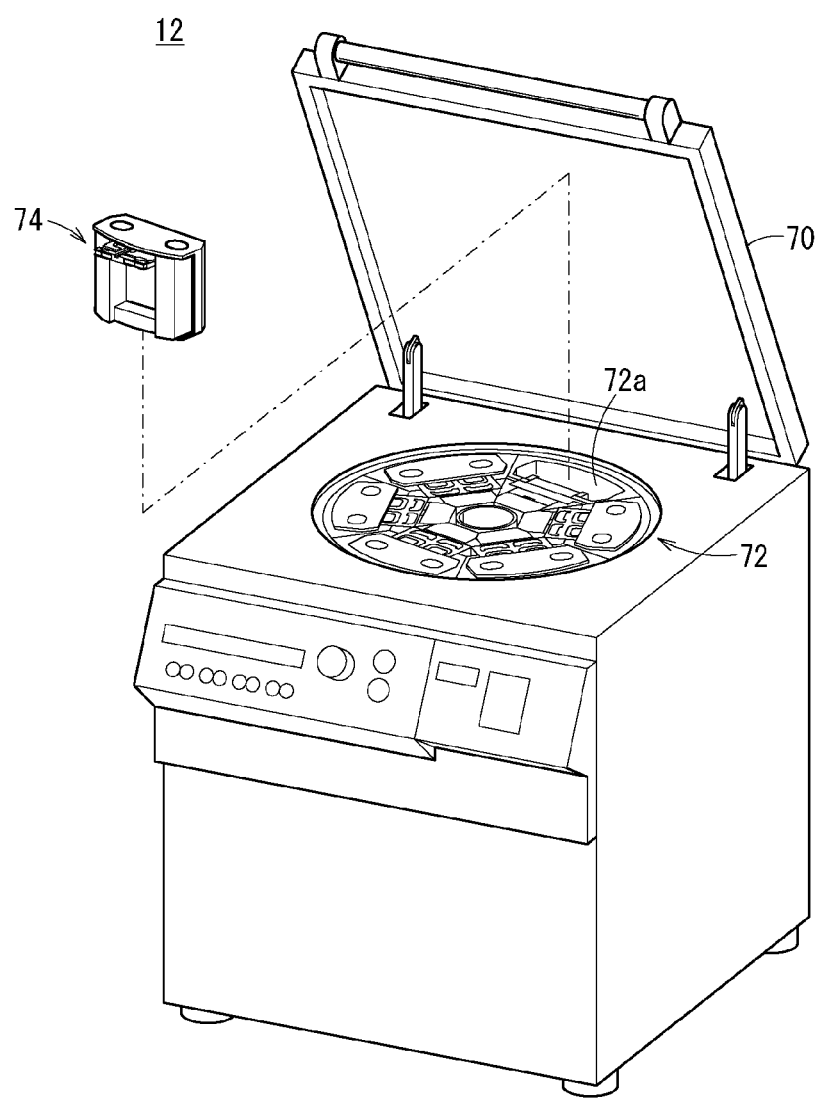
FIG. 4 is a perspective view of a blood product device that accommodates a blood bag system.

As illustrated in FIG. 4, the blood product device 12 has a box shape, and includes an openable/closable top surface cover 70, an internal centrifugal drum 72 (centrifugal separation means), six unit insertion holes 72a provided at equal angles (60°) in the centrifugal drum 72, six insert units 74 to be inserted to the respective unit insertion holes 72a, and six plungers 76 (pressing means: see FIG. 5) provided in a central portion and advanceable/retractable to/from the respective insert units 74 in a rotation radial direction.

Figure 5:
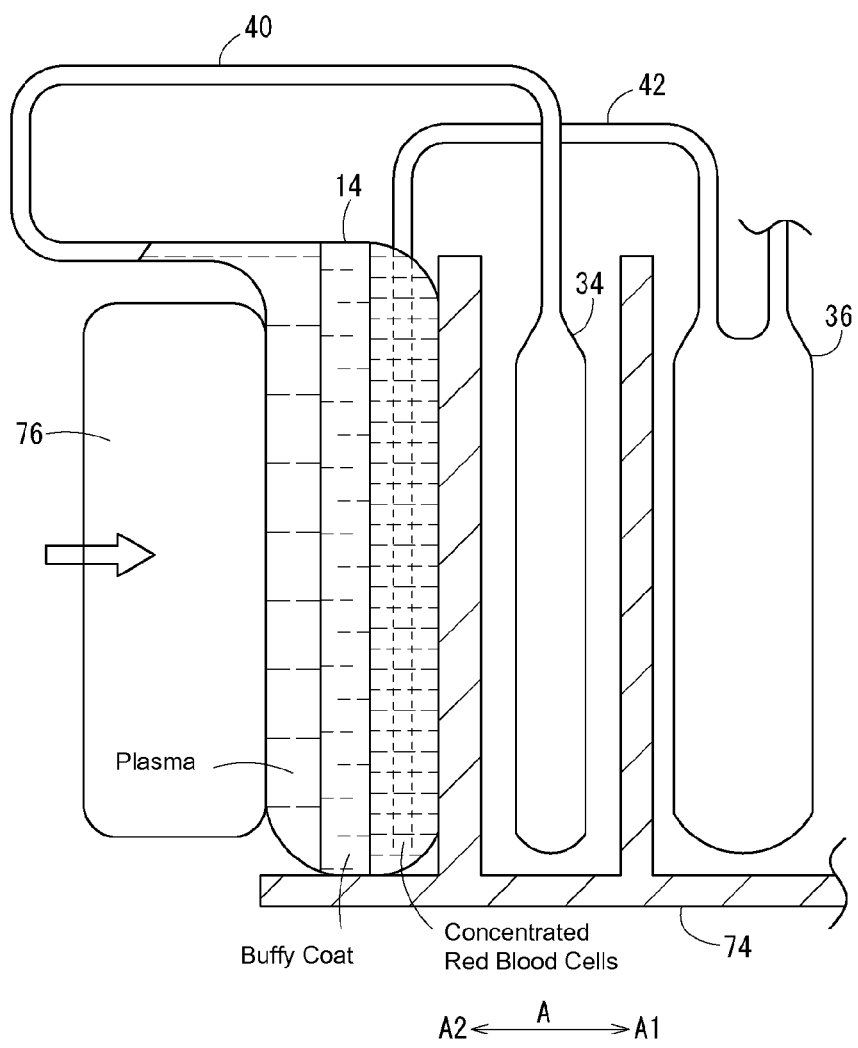
FIG. 5 is a diagram for describing a function in the blood product device of FIG. 4.

The blood bag system 26 is mounted to one insert unit 74 in a connected state with the bags and the tubes, and the insert unit 74 is inserted to the unit insertion hole 72a of the centrifugal drum 72. The centrifugal drum 72 rotates the insert unit 74 at a predetermined speed, thereby to provide centrifugal force to the blood bag 14 of the blood bag system 26. As a result, as illustrated in FIG. 5, the whole blood is separated in the blood bag 14.

In the transfer step after the centrifugation step, the plunger 76 is pushed toward the blood bag 14 (external diameter direction) while providing the centrifugal force. Accordingly, the plasma is transferred to the plasma bag 34 through the first tube 40, and the concentrated red blood cells are transferred to the RC-SAGM bag 36 through the second tube 42.

When the transfer step is terminated, the first and the second tubes 40 and 42 are sealed with the tube sealer or the like and cut out at positions close to the blood bag 14, so that the blood bag 14 becomes in a close state where the blood bag 14 stores the buffy coat. Then, the blood bag 14 is used in the next BC pooling in a state of being attached to the cassette 16.

Referring back to FIGS. 1 and 2, in the BC pooling, the pooling tube 20, the connector 28, and the BC bag 22 are connected in a state where the plurality of bag assemblies 18 is hung from the hanging tool 24. Accordingly, the medical bag handling system 10 is built, and transfer of the buffy coat from the blood bag 14 to the BC bag 22 becomes possible.

Then, the medical bag handling system 10 according to the present embodiment mutually connects the plurality of bag assemblies 18 in performing the BC pooling, thereby to able to integrally handle (hang) the bag assemblies 18, as illustrated in FIG. 2. Schematically speaking, the connecting means 32 is provided in the cassette 16 of the bag assembly 18, so that the cassettes 16 are connected and fixed, and a group of integrated bag assemblies 18 is built.

Figure 6:
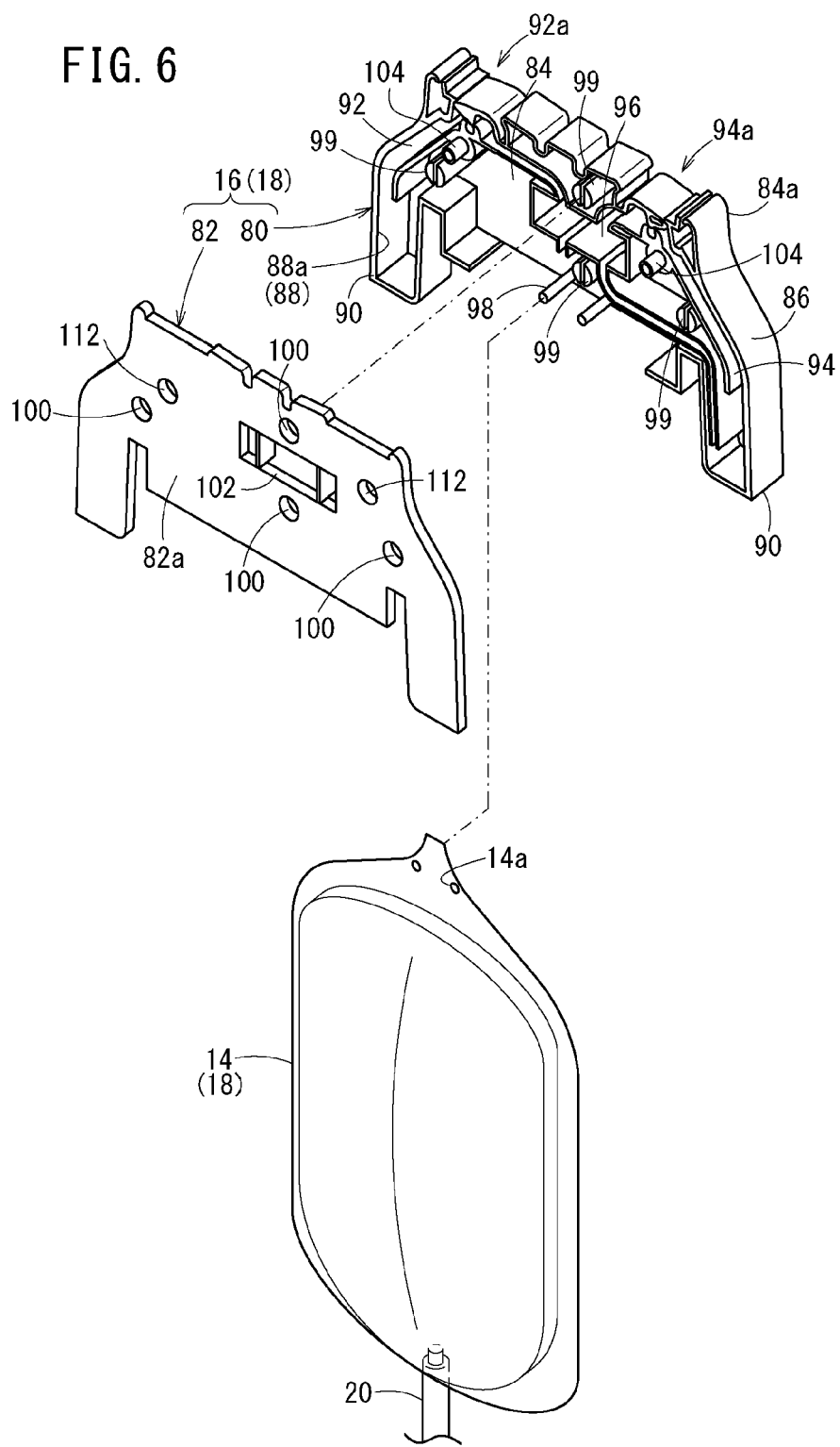
FIG. 6 is an exploded perspective view of the bag assembly of FIG. 2.

Therefore, in the following description, the connecting means 32 of the bag assembly 18 will be described in detail based on a relationship with the configuration of the cassette 16 with reference to FIGS. 2, 6 and 7.

The cassette 16 is configured from a cassette main body 80 that supports the blood bag 14, and a cover body 82 mounted on one surface of the cassette main body 80. Note that, in the following description, for convenience of description, a side of the cassette 16 to which the cover body 82 is attached is called front side (forward, front surface), and a side of a bottom wall 84 of the cassette main body 80, the side facing the cover body 82, is called rear side (rearward, rear surface). That is, the rear surface of the cassette 16 is a rear surface 84a (one planar portion) of the bottom wall 84, and the front surface of the cassette 16 is a front surface 82a (the other planar portion) of the cover body 82.

The cassette main body 80 is formed into a box shape with a bottom including an internal space 88 by the bottom wall 84 and a side wall 86 that surrounds a periphery of the bottom wall 84. An opposite surface of the bottom wall 84 is an opening portion 88a in which the internal space 88 extends, and the cover body 82 is attached to the opening portion 88a.

The bottom wall 84 is formed in an approximately trapezoidal shape with a narrow upper portion in a width direction and a wide lower portion in the width direction, and side portions having a similar length (equal sides), in plan view (see FIG. 1). A pair of extension portions 90 protruding downward by a predetermined length is formed at both side portions in the width direction, of a lower portion side. A planar shape of the cassette main body 80 corresponds to the shapes of the centrifugal drum 72 of the blood product device 12 and the insert unit 74.

First and second guide passages 92 and 94 that allow the above-described first and second tubes 40 and 42 to be arranged, and fix and hold the tubes 40 and 42 are formed in a front surface of the bottom wall 84. The first and second guide passages 92, 94 are configured such that a plurality of walls provided on the bottom wall 84 forms grooves together with the side wall 86. One of the pair of extension portions 90 is a holding portion that holds a taking-out portion of the first tube 40, and the other of the pair of extension portions 90 is a holding portion that holds a taking-out portion of the second tube 42. Further, first and second clamp mechanisms 92a and 94a that can operate open and close of the first and second tubes 40 and 42 are provided in intermediate positions (predetermined positions of the side wall 86) of the first and second guide passages 92 and 94. Note that the first and second tubes 40 and 42 are cut out after the transfer step, as described above. Therefore, the first and second tubes 40 and 42 are removed from the first and second guide passages 92 and 94 at the time of the BC pooling.

Further, a sensor mouth portion 96 is formed penetrating a central portion of the bottom wall 84. A detection sensor (not illustrated) is inserted to the sensor mouth portion 96 when the blood bag system 26 is attached to the insert unit 74. The detection sensor individually detects the plasma circulated in the first tube 40 and the concentrated red blood cells circulated in the second tube 42. The blood product device 12 controls the centrifugal separation, based on a detection result of the detection sensor.

A pair of pins 98 is formed on a central portion of the bottom wall 84 close to a lower portion. These pins 98 are inserted to attaching holes 14a provided in an upper portion of the blood bag 14, and hang and support the blood bag 14. Note that the blood bag 14 stores the buffy coat separated from the whole blood, and is thus supported by the cassette 16 in a state where the thickness of the blood bag 14 in a front and rear direction is thinner than the thickness of the cassette main body 80 (a protruding height of the side wall 86).

Further, a plurality of (four in the present embodiment) attaching terminals 99 to be connected with the cover body 82 is formed on the front surface of the bottom wall 84. A pair of the attaching terminals 99 is provided on upper and lower central portions in the width direction in plan view, and a pair of the attaching terminals 99 is provided on right and left central portions in an up and down direction. The attaching terminals 99 are attached to the four places on the bottom wall 84, so that the cassette main body 80 and the cover body 82 are firmly connected. Further, a central portion of the attaching terminal 99 is notched, so that the attaching terminal 99 is divided as a pair of hooks. The cover body 82 can be relatively easily removed by close operation of the pair of hooks.

The rear surface 84a of the bottom wall 84 is approximately entirely formed in a planar manner, and can be closely attached to the front surface 82a of the cover body 82.

The cover body 82 is formed in a flat plate shape approximately coinciding with the shape of the cassette main body 80. At the times of the centrifugation step and the transfer step, the internal space 88 of the cassette main body 80 is covered by the cover body 82, so that the first and second tubes 40 and 42 fixed to and held by the first and second guide passages 92 and 94 are protected. The cover body 82 is favorably formed transparent, and thus states of the plasma and the concentrated red blood cells circulated in the first and second tubes 40 and 42 can be visually recognized, accordingly.

Mounting holes 100 are provided in positions facing the attaching terminals 99 (that is, upper, lower, right, and left positions) in a planar portion of the cover body 82, and a window portion 102 is provided in a position facing the sensor mouth portion 96. The attaching terminals 99 are inserted to the mounting holes 100, and the pairs of hooks are hung on peripheral edge portions of the mounting holes 100, so that the cover body 82 and the cassette main body 80 are attached. In this attached state, the sensor mouth portion 96 and the window portion 102 overlap with each other in a layering direction and communicate into each other.

Then, the connecting means 32 of the cassette 16 is configured from a portion to be engaged with another cassette 16, and an engaging portion that holds (engages) the portion to be engaged of still another cassette 16. These portion to be engaged and engaging portion are provided in the bottom wall 84 of the main body of the cassette 16.

Specifically, as illustrated in FIGS. 6, and 7A to 7C, a protruding portion 104 formed in a cylindrical manner protruding in a forward direction is integrally formed (provided in a linked manner) with the bottom wall 84. A pair of the protruding portions 104 is provided in an upper portion side of the cassette main body 80, and close to both side portions in the width direction of the cassette main body 80 (positions inside and near the first and second guide passages 92 and 94 formed along the side wall 86).

A through hole 106 penetrating along an axial direction (a thickness direction of the cassette 16) is formed inside the protruding portion 104. The through hole 106 is used to perform positioning of the bag assembly 18, by being inserted to a projection (not illustrated) of the blood product device 12 when the insert unit 74 is set to the blood product device 12.

The protruding portion 104 is formed to have different thicknesses (outer diameters) along a protruding direction. That is, the protruding portion 104 is configured from a base cylinder portion 108 with a large diameter connecting to the bottom wall 84, and a tip cylinder portion 110 with a smaller diameter than the base cylinder portion 108 at a tip side of the base cylinder portion 108. The base cylinder portion 108 is formed to have a length so as to be positioned in the internal space 88 of the cassette main body 80, and the tip cylinder portion 110 continuously protrudes to have a difference in level from the base cylinder portion 108 by a predetermined amount.

Figure 7A:
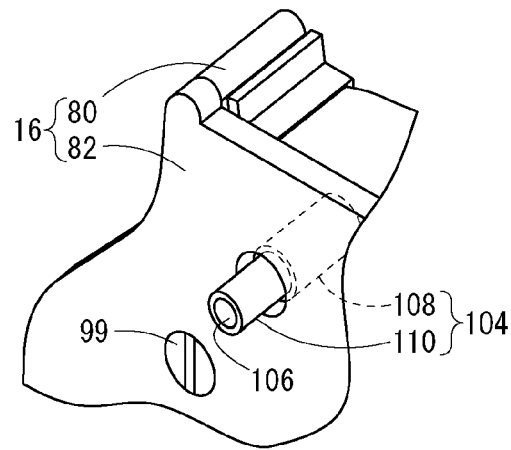
FIG. 7A is a partial perspective view for describing connecting means of a cassette of FIG. 2.
Figure 7B:
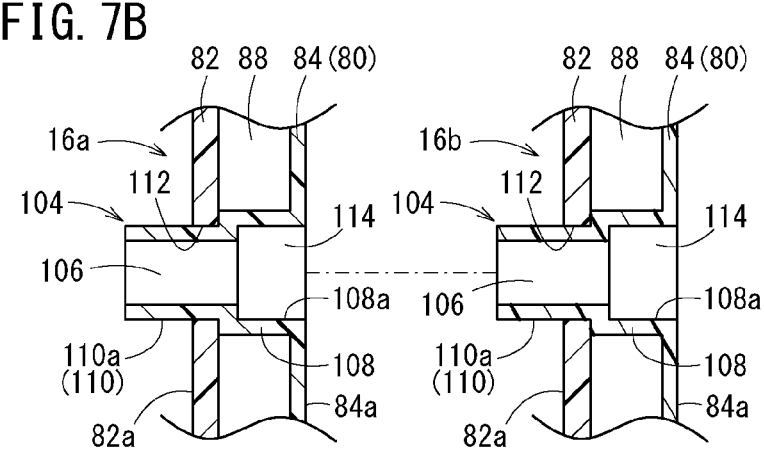
FIG. 7B is a first sectional view for describing connection of the cassette of FIG. 2.

Meanwhile, the cover body 82 includes an inserting hole 112 in a position overlapping with the protruding portion 104 in the layering direction. The inserting hole 112 is formed to have a slightly larger diameter than an outer diameter of the tip cylinder portion 110, through which the tip cylinder portion 110 penetrates and is inserted. In the attached state of the cassette main body 80 and the cover body 82, as illustrated in FIGS. 7A and 7B, the tip cylinder portion 110 penetrates the cover body 82, and protrudes from the front surface 82a of the cover body 82. The tip cylinder portion 110 and the inserting hole 112 also guide the positioning in a surface direction when the cover body 82 is attached to the cassette main body 80.

The through hole 106 of the protruding portion 104 has different inner diameters according to the thicknesses of the base cylinder portion 108 and the tip cylinder portion 110. That is, the inner diameter of the through hole 106 configured from an internal surface 108a of the base cylinder portion 108 is formed larger than the internal diameter of the through hole 106 configured from an internal surface of the tip cylinder portion 110.

Especially, the inner diameter of the through hole 106 at the side of the base cylinder portion 108 is configured to coincide with the outer diameter of the tip cylinder portion 110. The depth of the through hole 106 at the side of the base cylinder portion 108 approximately coincides with the protruding amount of the tip cylinder portion 110 protruding from the front surface of the cover body 82. Therefore, the through hole 106 at the side of the base cylinder portion 108 can allow and lock insertion of the tip cylinder portion 110 (hereinafter, the through hole 106 at the side of the base cylinder portion 108 is referred to as locking hole 114). Note that the through hole 106 at a forward side of the locking hole 114 may be blocked because this portion of the through hole 106 is not especially used as the connecting means 32. In this case, the connecting means 32 includes a recessed portion (locking recessed portion: engaging portion) (not illustrated) having a function of the locking hole 114. The recessed portion can be appropriately applied in first to sixth modifications below.

Figure 7C:
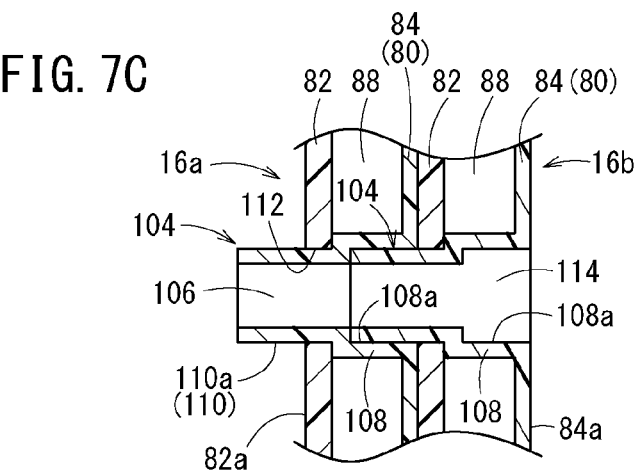
FIG. 7C is a second sectional view for describing the connection of the cassette of FIG. 2.

In other words, the connecting means 32 of the cassette 16 is configured from the protruding portion 104 (an external surface 110a of the tip cylinder portion 110), which is the portion to be engaged, and the locking hole 114 (the internal surface 108a of the through hole 106) of the protruding portion 104, which is the engaging portion. As illustrated in FIGS. 7B and 7C, when two cassettes 16 (a first cassette 16a and a second cassette 16b) are connected, the tip cylinder portion 110 of the second cassette 16b is inserted to the locking hole 114 of the front-side first cassette 16a. With the insertion, the external surface 110a of the tip cylinder portion 110 comes in contact with the internal surface 108a of the locking hole 114 with large friction force. Therefore, the locking hole 114 and the tip cylinder portion 110 are fit to each other, and unexpected dropping out of the tip cylinder portion 110 from the locking hole 114 can be prevented.

Further, the first cassette 16a and the second cassette 16b are formed to have the same shape. Therefore, in a state where the first cassette 16a and the second cassette 16b are layered and arranged in the thickness direction, the tip cylinder portion 110 is arranged in a position facing the locking hole 114. Therefore, the cassettes 16 are brought to come close to each other, so that the pairs of the tip cylinder portions 110 and the locking holes 114 provided at both sides in the width direction can be connected at the same time. The first cassette 16a and the second cassette 16b are connected at two places at both sides in the width direction, thereby to firmly hold each other.

Further, the second cassette 16b exposes the locking hole 114 formed in the rear surface 84a of the cassette main body 80. Therefore, the locking hole 114 is engaged with the tip cylinder portion 110 of another cassette (a third cassette 16c: see FIG. 2), so that the second cassette 16b and the third cassette 16c can be connected.

The medical bag handling system 10 and the cassette 16 according to the present embodiment are basically configured as described above. Hereinafter, functions and effects will be described.

The medical bag handling system 10 is configured at the time of the BC pooling, as described above (see FIG. 1). In the BC pooling, the pooling tube 20 is connected with a plurality (three) of bag assemblies 18 to configure a tube circuit leading to the one BC bag 22.

At the time of the BC pooling, the bag assembly 18 is in a state where the first and second tubes 40 and 42 connected at the time of the centrifugal separation are removed and the cassette 16 simply supports the blood bag 14. Further, the cover body 82 is attached to the opening portion 88a of the cassette main body 80. Therefore, the tip cylinder portion 110 of the protruding portion 104 is in a protruding state from the front surface 82a of the cover body 82 by a predetermined length (see FIG. 7A).

Then, in the medical bag handling system 10, the cassettes 16 of the three bag assemblies 18 are connected, so that a supply side of the buffy coat is integrally handled. That is, the three bag assemblies 18 are connected to face each other with the connecting means 32 provided in the cassettes 16.

Specifically, as illustrated in FIGS. 7B and 7C, the tip cylinder portion 110 of the cassette 16 arranged at a rear side is inserted to the locking hole 114 of the cassette 16 arranged at a front side, so that the locking hole 114 and the tip cylinder portion 110 are fit. Accordingly, the three cassettes 16 are connected with each other in the thickness direction (the mutual planar portions are layered), so that the cassettes 16 can be handled as an integral supply source. Note that, at the time of the BC pooling, the blood bag 14 is thinner than the thickness of the cassette 16. Therefore, the bag assemblies 18 cannot come off due to interference between the bags for blood 14.

Then, as illustrated in FIG. 2, a user hangs the three bag assemblies 18 from the hanging tool 24 through the hook member 30 in the connection state of the cassettes 16. At this time, the three bag assemblies 18 are layered in the layering direction, and thus can be hung from the hanging tool 24 without taking a space.

In the BC pooling, the three bag assemblies 18 are hung at the same height position. Therefore, the buffy coat can be sent from the respective bags for blood 14 in a uniform manner. Therefore, the buffy coat can be favorably transferred to the BC bag 22.

After the BC pooling, cleaning operation of the used bags for blood 14 is performed. In the cleaning operation, a cleaning solution is brought to flow into each blood bag 14 through the pooling tube 20 and insides of the bags for blood 14 are cleaned. Even in this case, the three bag assemblies 18 are connected and held at the same height, and thus the cleaning solution can be uniformly transferred to the bags for blood 14. Therefore, the cleaning can be favorably performed.

As described above, according to the medical bag handling system 10 and the cassette 16 according to the present embodiment, the cassettes 16 can be connected with the simple structure including the connecting means 32. As a result, the bags for blood 14 respectively supported by the cassettes 16 can be collectively handled. For example, when a plurality of the bags for blood 14 is used at the time of the BC pooling, these bags for blood 14 can be easily handled. Therefore, work efficiency is improved. Further, a decrease in the space can be achieved by the collective handling of the bag assemblies 18 (cassettes 16), and work can be favorably performed even in a small space.

In this case, the connecting means 32 is configured from the protruding portion 104 formed on the front surface 82a of the cassette 16 and the locking hole 114 formed in the rear surface. Therefore, the cassettes 16 can be easily connected and layered in the thickness direction. Accordingly, the plurality of bags for blood 14 can be arranged and connected, and handling thereof can become easier.

Further, the connecting means 32 is configured from the engagement structure of the protruding portion 130 and the locking hole 114. Therefore, the planer portions of the cassettes 16 are brought to come close to each other in a state where the planer portions coincide with each other in the layering direction, whereby the cassettes 16 can be easily connected.

Note that the medical bag handling system 10 and the cassette 16 according to the present invention are not limited to the above-describe embodiment, and it is apparent that various configurations can be employed. Hereinafter, some modifications of the present invention will be described. Note that, in the description below, the same configurations and configurations having the same functions as the medical bag handling system 10 and the cassette 16 of the present embodiment are denoted with the same reference signs, and detailed description thereof is omitted.

Figure 8A:
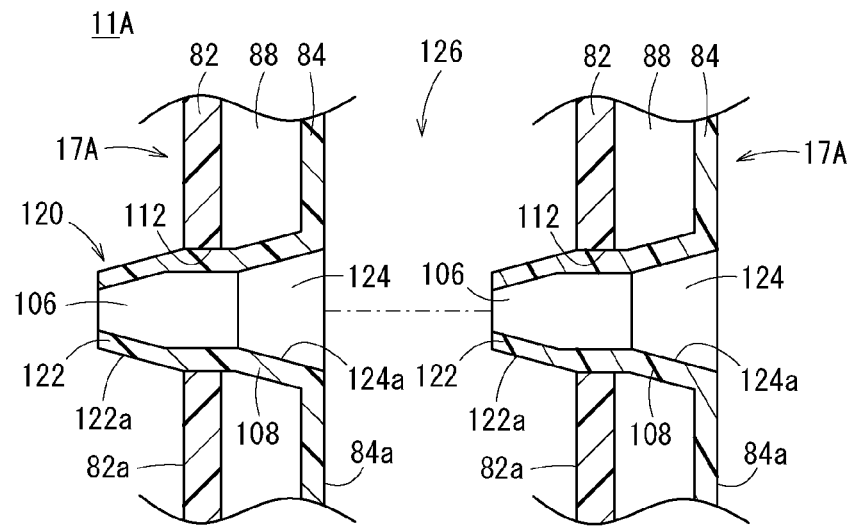
FIG. 8A is a first sectional view for describing connection of a cassette of a medical bag handling system according to a first modification.
Figure 8B:
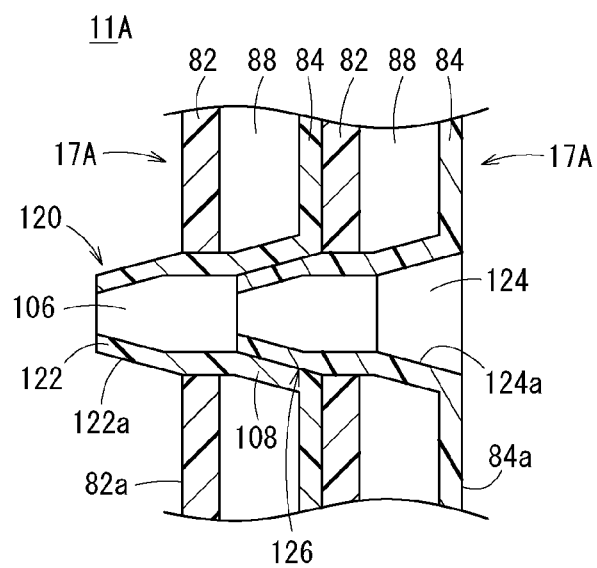
FIG. 8B is a second sectional view for describing the connection of the cassette of the medical bag handling system according to the first modification.

A cassette 17A (medical bag handling system 11A) according to a first modification illustrated in FIGS. 8A and 8B has a configuration in which an external surface of a tip cylinder portion 122 of a protruding portion 120 is formed into a tapered external surface 122a that becomes narrow in a tip direction. Further, an internal surface of a locking hole 124 of the protruding portion 120 (through hole 106) is also formed into a tapered internal surface 124a that becomes narrow in a depth direction, corresponding to the external surface 122a. Therefore, when the tip cylinder portion 122 is inserted to the locking hole 124, the tapered external surface 122a of the tip cylinder portion 122 and the tapered internal surface 124a of the locking hole 124 can be taper fit. As descried above, connecting means 126 (the protruding portion 120 and the locking hole 124) can favorably connect the cassettes 17A even if formed to have a tapered surface.

Figure 9A:
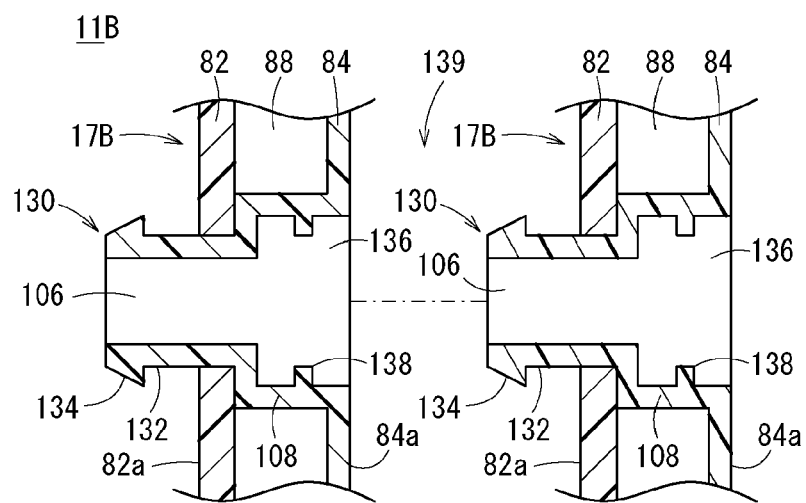
FIG. 9A is a first sectional view for describing connection of a cassette of a medical bag handling system according to a second modification.
Figure 9B:
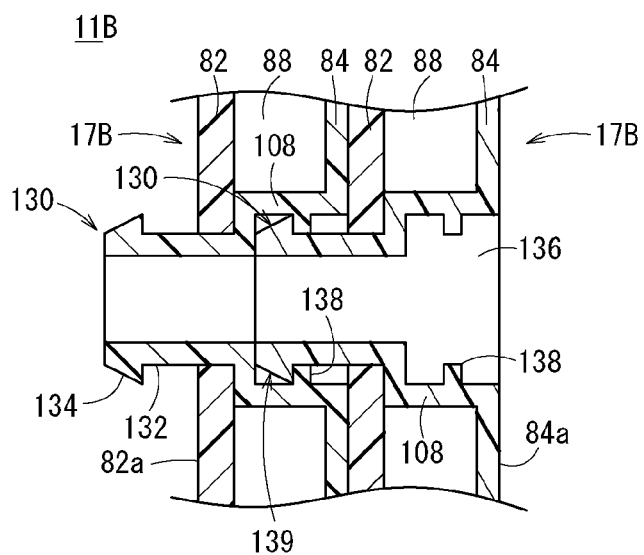
FIG. 9B is a second sectional view for describing the connection of the cassette of the medical bag handling system according to the second modification.

A cassette 17B (medical bag handling system 11B) according to a second modification illustrated in FIGS. 9A and 9B has a configuration in which a claw portion 134 is provided to a tip cylinder portion 132 of a protruding portion 130. The claw portion 134 is formed in a ring manner along a circumferential direction at a forwardmost side of the tip cylinder portion 132. Meanwhile, a projecting portion 138 that can hang the claw portion 134 is formed along the circumferential direction on an internal surface of a locking hole 136 of the protruding portion 130 (through hole 106). Therefore, when the tip cylinder portion 132 is inserted to the locking hole 136, the claw portion 134 is hung on the projecting portion 138 of the locking hole 136, and the tip cylinder portion 132 can be prevented from being pulled out. As described above, connecting means 139 (the protruding portion 130 and the locking hole 136) can more reliably connect the cassettes 17B with the hanging structure with the claw portion 134 and the projecting portion 138.

Figure 10A:
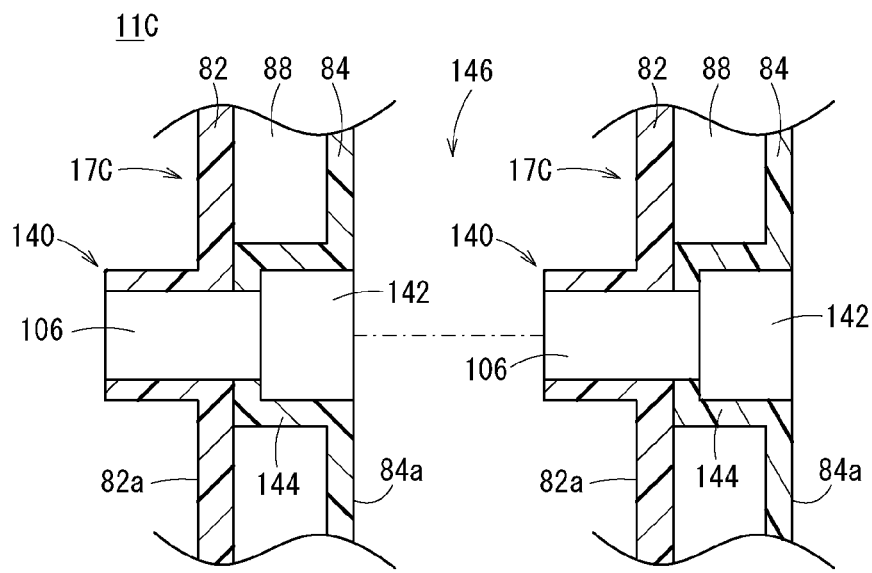
FIG. 10A is a first sectional view for describing connection of a cassette of a medical bag handling system according to a third modification.
Figure 10B:
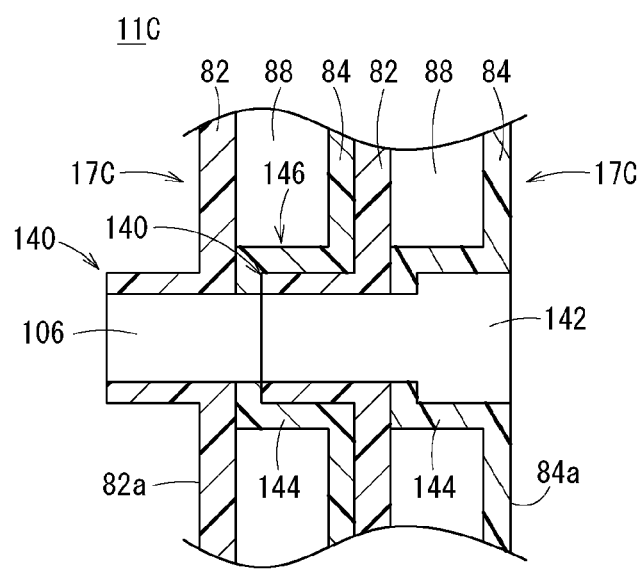
FIG. 10B is a second sectional view for describing the connection of the cassette of the medical bag handling system according to the third modification.

A cassette 17C (medical bag handling system 11C) according to a third embodiment illustrated in FIGS. 10A and 10B has a configuration in which a protruding portion 140 is provided to a cover body 82. Further, a locking protrusion 144 having a locking hole 142 that locks the protruding portion 140 is formed forward in a protruding manner in a bottom wall 84 of a cassette main body 80. That is, in connecting means 146 according to the third modification, the protruding portion 140 of the cover body 82 is inserted and fit to the locking hole 142 of the locking protrusion 144, so that the cassettes 17C are connected. As described above, the connecting means 146 may separately provide the protruding portion 140 and the locking hole 142 to the cassette main body 80 and the cover body 82. This is because the cassette main body 80 and the cover body 82 are firmly assembled with attaching terminals 99 and mounting holes 100, as described above.

Figure 11A:
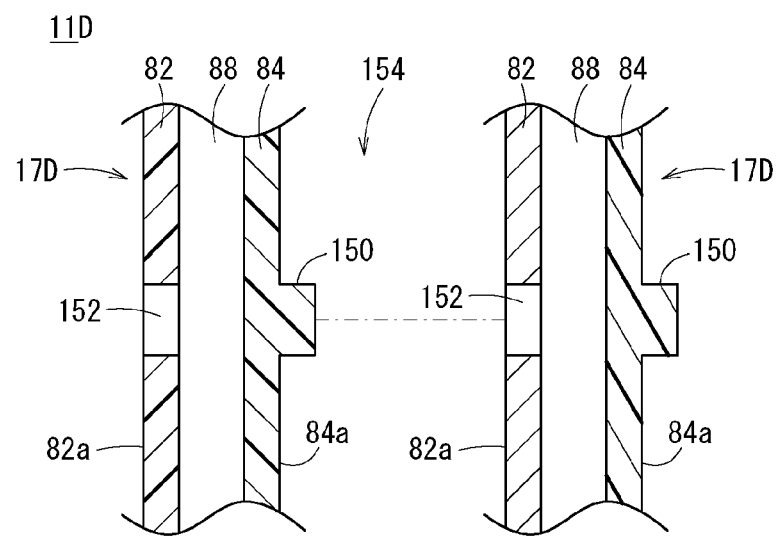
FIG. 11A is a first sectional view for describing connection of a cassette of a medical bag handling system according to a fourth modification.
Figure 11B:
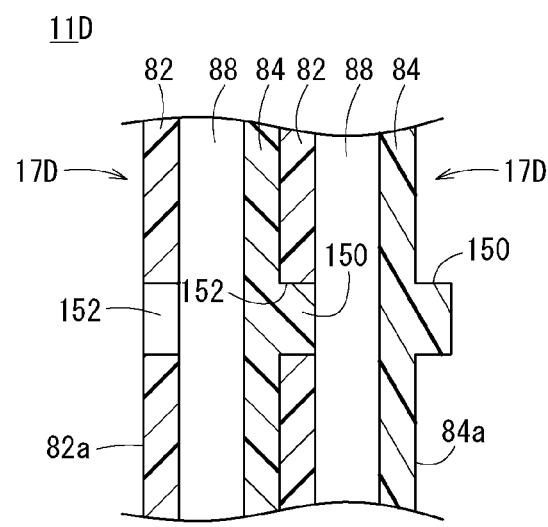
FIG. 11B is a second sectional view for describing the connection of the cassette of the medical bag handling system according to the fourth modification.

A cassette 17D (medical bag handling system 11D) according to a fourth modification illustrated in FIGS. 11A and 11B has a configuration in which a protruding portion 150 is provided on a rear surface 84a of a cassette main body 80. Further, a locking hole 152 that locks the protruding portion 150 is formed in a cover body 82. That is, in connecting means 154 according to the fourth modification, the protruding portion 150 of the cassette main body 80 is inserted and fit to the locking hole 152 of the cover body 82, so that the cassettes 17D are connected. As described above, the connecting means 154 may have the configuration in which the protruding portion 150 that is a portion to be engaged is provided at a side of the rear surface 84a of the cassette 17D, and the locking hole 152 that is an engaging portion is provided at a side of a front surface 82a of the cassette 17D. In short, forming surfaces of the portion to be engaged and the engaging portion in the cassette is not especially limited.

Figure 12:
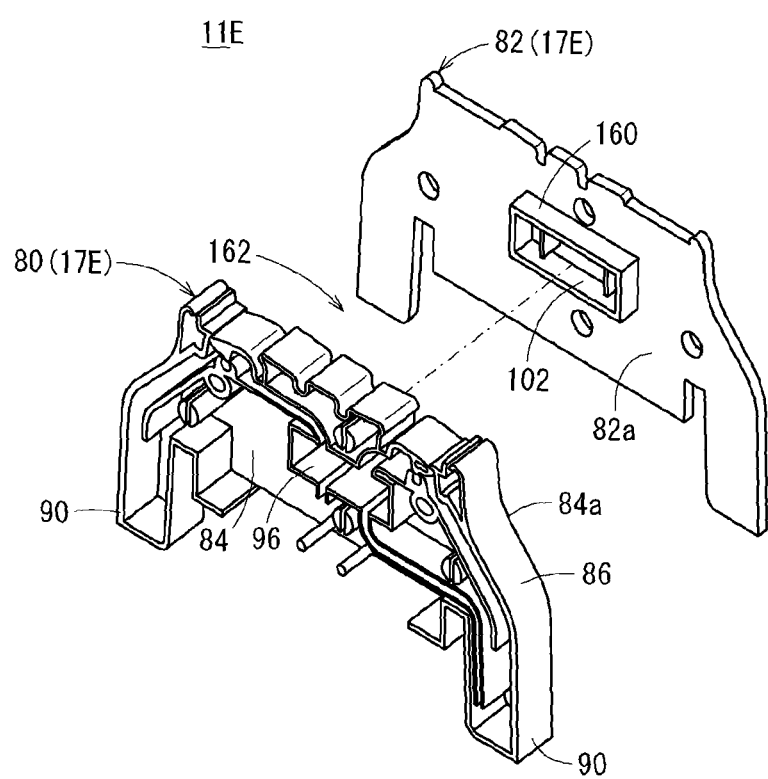
FIG. 12 is a partial perspective view for describing connection of a cassette of a medical bag handling system according to a fifth modification.

A cassette 17E (medical bag handling system 11E) according to a fifth modification illustrated in FIG. 12 has a configuration in which a protruding portion 160 is provided on a peripheral edge portion of a window portion 102 formed on a cover body 82. The protruding portion 160 is formed to be able to be inserted and fit to a sensor mouth portion 96 (locking hole) formed in a cassette main body 80. As described above, connecting means 162 (the protruding portion 160 and the sensor mouth portion 96) can be configured using the shapes provided in the cassette in advance, and shapes of an engaging portion and a portion to be engaged can be appropriately designed.

Figure 13A:
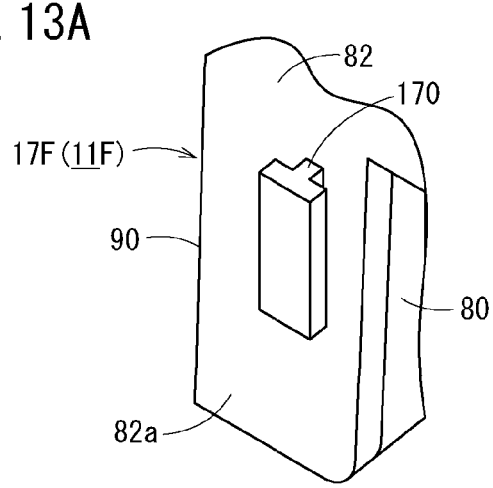
FIG. 13A is a perspective view illustrating a partially enlarged cassette of a medical bag handling system according to a sixth modification.
Figure 13B:
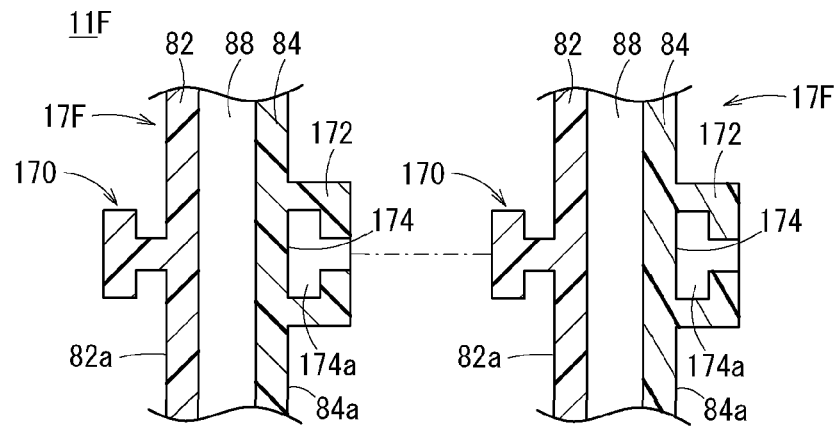
FIG. 13B is a first sectional view for describing connection of the cassette of the medical bag handling system according to the sixth modification.
Figure 13C:
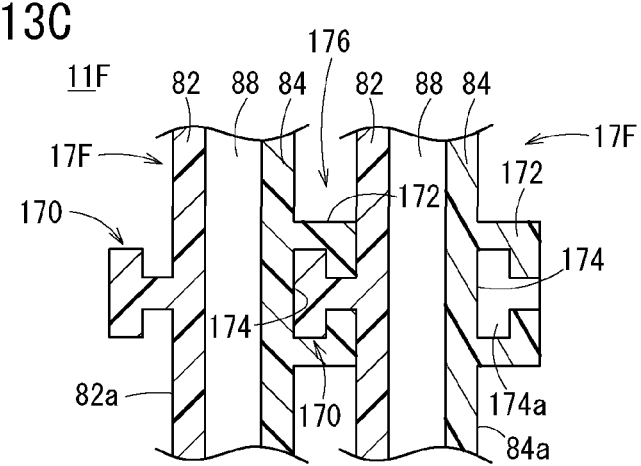
FIG. 13C is a second sectional view for describing the connection of the cassette of the medical bag handling system according to the sixth modification.

A cassette 17F (medical bag handling system 11F) according to a sixth modification illustrated in FIGS. 13A to 13C has a configuration in which a protruding portion 170 is provided on a front surface 82a of a cover body 82 (a pair of extension portions 90 of a cassette 17F). The protruding portion 170 is formed in a T-shaped manner in section view, and is formed in an up and down direction of the extension portion 90 by a predetermined length. Meanwhile, a holding portion 172 that can hold the protruding portion 170 is formed on a rear surface 84a of a cassette main body 80. The holding portion 172 includes a groove portion 174 corresponding to the T-shape of the protruding portion 170, and the groove portion 174 is formed such that an upper portion is open, and a lower portion is closed with a bottom portion 174a.

Therefore, the protruding portion 170 is downwardly inserted and slid to the groove portion 174 of the holding portion 172 from an upper side, so that connecting means 176 can connect the cassettes 17F. In this case, connection between the cassettes 17F can be more reliably performed because the T-shaped protruding portion 170 and the groove portion 174 are hung in a layering direction. Further, to cancel a connection state, the connection state can be easily cancelled by upwardly pulling the cassette 17F of a rear side along the groove portion 174 of the cassette 17F of a front side.

Figure 14:
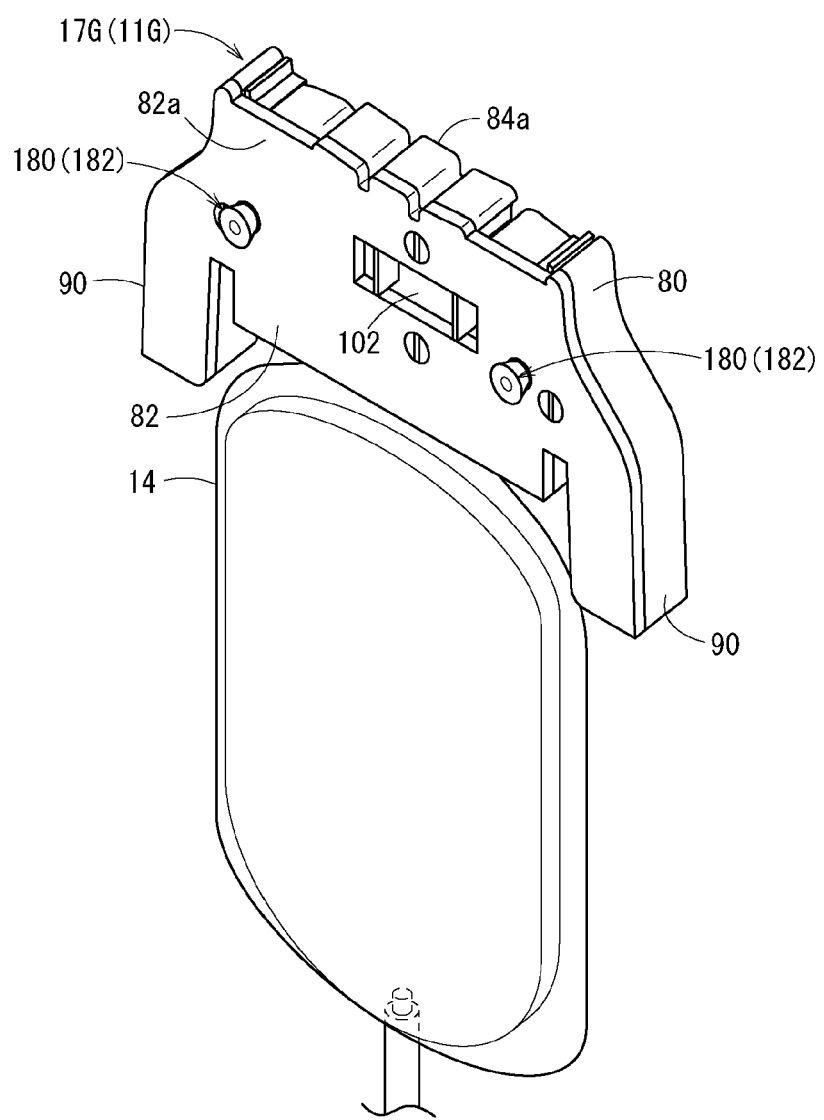
FIG. 14 is a perspective view for describing a cassette of a medical bag handling system according to a seventh modification.

A cassette 17G (medical bag handling system 11G) according to a seventh modification illustrated in FIG. 14 has a configuration in which a pair of suction pads 180 is provided on a front surface 82a of a cover body 82. Meanwhile, portions facing the suction pads 180, of a rear surface 84a of a cassette main body 80 are formed in a planar surface (not illustrated). That is, connecting means 182 of the cassette 17G is realized by adsorption power to a protruding direction (thickness direction) of the suction pads 180. As described above, a plurality of bag assemblies 18 can be integrally handled with the suction pads 180.

Figure 15B:
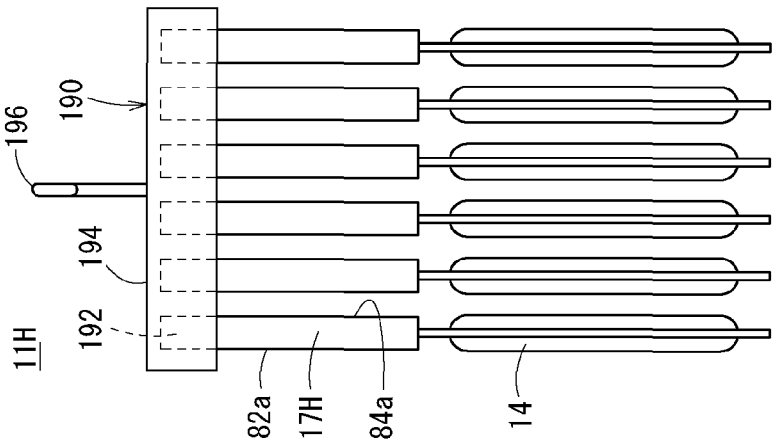
FIG. 15B is a side view for describing the connection of the cassette of the medical bag handling system according to the eighth modification.
Figure 15A:
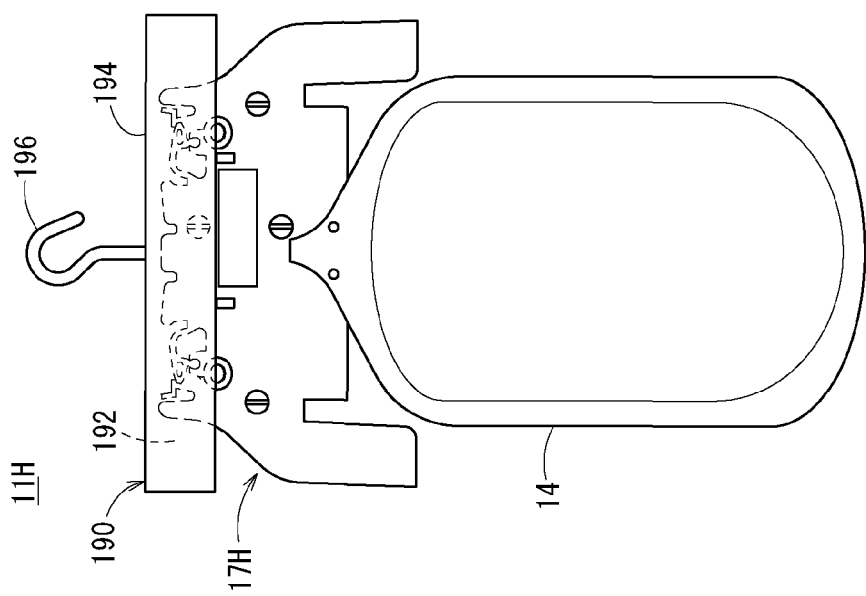
FIG. 15A is a front view for describing connection of a cassette of a medical bag handling system according to an eighth modification.

A medical bag handling system 11H according to an eighth modification illustrated in FIGS. 15A and 15B has a configuration in which any connecting means is not provided in a cassette 17H, and a plurality of the cassettes 17H is connected by a connection device 190 (connecting means) that can hold the cassettes 17H. The connection device 190 includes a plurality of (six in FIG. 15B) holding spaces 192 that holds upper portions of the cassettes 17H along a front and rear direction.

A lower surface side of one holding space 192 is open, and a frame body 194 that configures the holding space 192 is formed with a width that can hold a front surface and a rear surface of the upper portion of the cassette 17H with relatively large friction force. Therefore, when the cassette 17H is inserted from a lower surface side, the connection device 190 holds the cassette 17H with strong holding force. The plurality of holding spaces 192 can cause the plurality of cassettes 17H to be in a connected state in a thickness direction, and thus can integrally handle a plurality of bag assemblies 18. Further, a hook 196 is provided on an upper portion of the connection device 190, and the connection device 190 can be easily hung from a hanging tool 24 with the hook 196.

As described above, in the medical bag handling system 11H, a conventional cassette is applicable as the cassette 17H, by use of the connection device 190 for connecting the cassettes 17H, separately from the cassettes 17H. Therefore, an increase in cost by preparation of new cassettes can be suppressed. Note that the configuration of the connection device 190 is not limited to the above embodiment, and various configurations can be employed such as use of a clip that can integrally pinch the plurality of cassettes 17H.

Further, as a medical bag handling system according to another modification, a zipper (not illustrated) may be provided in an edge portion of a front surface 82*a* of a cover body 82 and a rear surface 84*a* of a cassette main body 80. The zipper connects cassettes, by being moved and operated along the edge portions in a state where the front surface and the rear surface of the cassettes are layered.

Favorable embodiments have been described about the present invention. However, the present invention is not limited to the above embodiments, and it is apparent that various changes can be made without departing from the gist of the present invention. For example, the medical bag handling system and the cassette are not applied only to performing of the BC pooling, and can be favorably used when a plurality of medical bags (including blood transfusion bags and the like, in addition to the bags for blood) is used.

The invention claimed is:

1. A medical bag handling system comprising:
  a plurality of medical bag holding cassettes at least some of said cassettes having a box shape with a thickness between front and rear sides and having planar areas on said front and rear sides;
  a coupling on at least one planar area on at least one cassette wherein the coupling is a hole or recess; and
  a mating coupling on at least one planar area of another cassette, said coupling and said mating coupling being adapted to connect with each other, wherein the mating coupling is a cylinder and
  wherein the cylinder has a tip cylinder portion having a first diameter and a base cylinder portion having a second diameter said second diameter being larger than said first diameter and
  wherein said base cylinder portion has a hole having an internal diameter coinciding with an external diameter of a tip cylinder portion on another cassette.

2. The medical bag handling system according to claim 1, further comprising a connecting means configured from a device capable of holding the plurality of medical bag holding cassettes in a state where the planar areas of adjacent cassettes face each other.

3. The medical bag handling system of claim 1 wherein said tip cylinder portion has a circumferential claw at a forward most side of said tip cylinder portion and
  wherein said hole in said base cylinder portion has a projecting portion.

\* \* \* \* \*